(12) United States Patent
Ally

(10) Patent No.: US 10,542,744 B2
(45) Date of Patent: Jan. 28, 2020

(54) CRYOGENIC STORAGE RACK INCLUDING ROTATABLE SHELVES, AND ASSOCIATED STORAGE SYSTEMS AND METHODS

(71) Applicant: Fisher BioServices Inc., Rockville, MD (US)

(72) Inventor: Abdul H. Ally, Gaithersburg, MD (US)

(73) Assignee: Fisher BioServices Inc., Rockville, MD (US)

( * ) Notice: Subject to any disclaimer, the term of this patent is extended or adjusted under 35 U.S.C. 154(b) by 295 days.

(21) Appl. No.: 15/484,662

(22) Filed: Apr. 11, 2017

(65) Prior Publication Data

US 2018/0292051 A1 Oct. 11, 2018

(51) Int. Cl.
*A01N 1/02* (2006.01)

(52) U.S. Cl.
CPC .................................. *A01N 1/0268* (2013.01)

(58) Field of Classification Search
CPC .... F16M 13/04; A47B 81/007; A47B 49/004; A01N 1/0257
USPC ........................ 220/560.04, 560.1; 211/115
See application file for complete search history.

(56) References Cited

U.S. PATENT DOCUMENTS

| 4,239,308 A * | 12/1980 | Bradley ................. A45C 11/16 312/201 |
| 6,648,390 B1 * | 11/2003 | Yang ...................... A47B 49/00 206/821 |
| 7,284,660 B2 * | 10/2007 | Smith .................... B23D 59/00 206/303 |
| 2009/0255288 A1 * | 10/2009 | Jia ............................ G01N 1/42 62/266 |
| 2009/0321451 A1 | 12/2009 | Byrne |
| 2011/0056902 A1 * | 3/2011 | Cognard .................. A01N 1/02 215/40 |
| 2013/0232998 A1 | 9/2013 | Ward et al. |

* cited by examiner

Primary Examiner — Jeffrey R Allen
(74) Attorney, Agent, or Firm — Wood Herron & Evans LLP

(57) ABSTRACT

A storage rack for storing and retrieving products to be maintained at a desired cryogenic temperature is provided. The storage rack includes an elongate mounting bar carrying a plurality of shelves, and an elongate stop bar that extends generally parallel to the mounting bar. The shelves are independently rotatable relative to the mounting bar towards and away from the stop bar, thereby enabling alignment of all of the shelves when the storage rack is to be stored, and also enabling easy access to each of the individual shelves. A handle projects upwardly and horizontally in a curved configuration from the stop bar and the mounting bar to provide a gripping surface for moving the storage rack. The shelves receive cylindrical vial containers with threadably removable lids to make retrieval and replacement of sample vials quick to perform, thereby avoiding temperature-induced damage to other samples in the storage rack.

20 Claims, 6 Drawing Sheets

CRYOGENIC STORAGE RACK INCLUDING ROTATABLE SHELVES, AND ASSOCIATED STORAGE SYSTEMS AND METHODS

TECHNICAL FIELD

The present invention relates generally to refrigerated storage systems and, more particularly, to storage racks configured to receive drug samples and/or biological samples for transport and cryogenic storage.

BACKGROUND

Biological and drug samples are often stored and/or transported for lengthy periods of time before use. To maintain the viability of such samples, the storage or transport units are typically configured with refrigeration systems or coolants that maintain an interior storage space at a desired temperature, typically a low or cryogenic temperature such as within a range of about −195° C. to about −40° C. The specific temperature depends on the samples being stored. In one example, stem cells to be used for research tests and activities are typically stored at about −195° C. to maintain the viability thereof. Allogeneic and autologous drug products may also be stored at similar temperatures, for example. As will be readily understood, any prolonged exposure of such samples to higher temperatures such as room temperatures can cause temperature-induced degradation that may ruin the samples. Therefore, it is important to store and handle these biological and drug samples in such a manner to avoid those temperature-induced degradations.

Storage of samples in cryogenic containers is typically done with one or more storage racks that hold and organize a plurality of samples. One conventional example of such a storage rack 300 is shown in FIG. 1. The storage rack 300 defines a rectangular box shape or cross section formed by a plurality of elongated side walls 302 and an open front surface, with a plurality of shelves 304 provided along the length of the side walls 302. The remainder of the rectangular box shape is generally solid, although there may be air flow apertures formed along the side walls 302 as well, to promote cold air flow through the storage spaces defined at the shelves 304. The storage spaces are sized to receive one or more sample storage boxes 306, which also define a generally rectangular cross section. The storage rack 300 of the conventional design further includes a small clip 308 along a top wall 310 which serves as a handle for moving the storage rack 300, and a retainer bar 312 that extends through apertures formed in the top wall 310 and in each of the plurality of shelves 304 along the open front surface to block the storage boxes 306 from falling out of the storage spaces. The storage rack 300 is typically received in a cylindrical storage sleeve 314 during storage in a cryogenic container, these elements being shown separated from one another in FIG. 1.

Although the storage rack 300 of the conventional design functions to organize and retain a number of product samples, the use and retrieval of product samples from the storage rack 300 often requires significant previous experience in order to perform these operations quickly. To this end, accessing one of the storage boxes 306 and the product sample(s) therein is a multi-step, relatively complicated process. More specifically, the storage rack 300 must first be pulled out of the storage sleeve 314, and this requires interaction with the small clip 308 that serves as a handle for the storage rack 300. It can be highly difficult to maintain a good grip on this clip 308 when moving the storage rack 300, as a result of its small size and low profile relative to the top wall 310. Next, a user must withdraw the retainer bar 312 by pulling it upwardly out of all of the apertures provided in the shelves 304 and the top wall 310. Only then can the storage box 306 be removed by the user for accessing one or more of the samples therein. The user must then return the retainer bar 312 into the inserted position and manipulate the storage rack 300 using the small clip 308 to re-insert the storage rack 300 back into the storage sleeve 314 for movement back into the cryogenic container. As can be readily understood from this description, this multi-step process can take a significant amount of time, particularly for users without significant experience with retrieving samples from these types of storage racks.

Moreover, the conventional design of the sample storage boxes 306 also presents some additional difficulties for users. In this regard, the storage boxes 306 are typically made from a plastic-like or cardboard-like material with openable lids and box ears, but these portions of the storage boxes 306 have a tendency to become brittle and snap off during opening or closing of the storage boxes 306, especially after storage in the cryogenic container at the desired temperature. This problem can negatively impact the reuse of the storage boxes 306, which is typically preferable in many fields. Furthermore, the opening and closing of the storage boxes 306 takes additional time, which can lead to the problems above with prolonged exposure of other samples to higher temperatures before the storage rack 300 can be replaced into the cryogenic container or environment.

For some types of biological and drug samples, thermal-induced degradation can begin after as little as 30 seconds of exposure to room temperatures outside the cryogenic container. Therefore, the significant amount of time needed to retrieve samples and storage boxes 306 from the storage rack 300 and then re-assemble and return the storage rack 300 to cryogenic storage presents a risk that the other samples will be degraded or damaged. Consequently, the conventional designs of storage racks present difficulties for users who need to store and retrieve a plurality of samples in an efficient storage space. While such disadvantages can be avoided by users with significant experience in retrieving the storage racks, it is not always possible to have users with significant experience, which can potentially lead to sample degradation and loss.

It is desirable, therefore, for further improvements in the cryogenic storage rack field and associated systems and methods for cryogenic sample storage, which address these and other deficiencies of known designs.

SUMMARY

According to one embodiment of the present invention, a storage rack is provided for retaining products in a cryogenic environment. The storage rack includes a framework having an elongate mounting bar and an elongate stop bar coupled to one another. The stop bar is spaced apart from and extends generally parallel to the mounting bar. A handle is coupled to at least one of the stop bar and the mounting bar, with the handle being configured to enable movement of the storage rack as a whole. The storage rack also includes a plurality of shelves pivotally coupled to the mounting bar so as to be individually and independently rotatable relative to an axis through the mounting bar towards and away from contact with the stop bar. Each of the plurality of shelves includes a bottom wall and a side wall collectively defining a container receptacle. When all of the plurality of shelves are rotated into contact with the stop bar, the plurality of shelves is aligned with one another for storage, such as within a cryogenic container such as a liquid nitrogen (LN2) storage canister. The handle and the individually rotatable shelves enable faster access to vial containers and samples contained on the storage rack because the storage rack can be manipulated or moved with one hand of a user while the other hand rotates a shelf out of alignment with the other shelves and then retrieves and/or replaces the vial container.

In one aspect, each of the plurality of shelves is configured to be rotated away from the stop bar and out of alignment with the other shelves to provide access into the container receptacle defined within the rotated shelf. To this end, the shelves can be rotated and reconfigured to a wide variety of positions relative to the framework of the storage rack. In another aspect, the side wall of each of the plurality of shelves defines a generally cylindrical shape, thereby making the container receptacles configured to receive a cylindrical vial container holding one of the products. In such embodiments, the side wall of the shelves may further include a top end positioned opposite the bottom wall, and at least one cutout extending downwardly towards the bottom wall provided at the top end. For example, opposing cutouts at opposite sides of the top end enables a user to grasp and lift a vial container out of the container receptacle. As with the rotation of the shelf, this retrieval step for the vial container can be done with a single hand in a time efficient manner.

The handle of the storage rack in some embodiments is coupled to both of the stop bar and the mounting bar. Accordingly, the handle extends between these elements of the framework to provide an enlarged gripping area for moving and manipulating the storage rack, preferably with one hand as described above. The handle advantageously projects horizontally and upwardly from top ends of the stop bar and the mounting bar to project over a portion of the plurality of shelves. More specifically, the handle defines a curved configuration to define the gripping area at the portion that projects from the top ends of the stop bar and the mounting bar. The large gripping area makes the storage rack easier to retrieve and control when moving the storage rack to and from a cryogenic storage.

In yet another aspect, the side wall of each of the shelves further includes a top end positioned opposite the bottom wall, and the storage rack further includes a lid element fixedly coupled to the stop bar. The lid element is located at a position adjacent the top end of an uppermost shelf when that uppermost shelf is rotated into contact with the stop bar. To this end, the lid element closes off or covers the top end of the container receptacle defined within the uppermost shelf when in the aligned configuration for storage. The bottom wall of each of the plurality of shelves also serves as a lid element for an adjacent shelf positioned immediately beneath the bottom wall, in a similar manner as the lid element at the top end of the uppermost shelf. Consequently, the vial containers are securely retained within the corresponding container receptacles. The lid element and the plurality of shelves may define clearance gaps between themselves of 0.1 inch or less, for example. In embodiments with at least four shelves pivotally coupled to the mounting bar, the bottom wall of the top three shelves will act as lid elements for the shelves located directly below, at least when the shelves are rotated so as to be aligned with one another in contact with the stop bar.

The storage rack is therefore easily manipulated and vial containers therein are easily retrieved, so that other product samples on the storage rack can be returned to a cryogenic environment quickly to avoid thermal-inducted degradation of samples. Moreover, such actions with the storage rack are intuitive for even those users without significant experience using the storage rack.

In another embodiment of the present invention, a storage system is provided for retaining products in a cryogenic environment. The storage system includes an outer sleeve element that is sized to be received in a cryogenic chamber, such as a liquid nitrogen-cooled storage tank. The system also includes a storage rack that is configured to hold the products and also configured to be inserted into the outer sleeve element during placement in the cryogenic chamber. The storage rack is similar to the one described above, such as by including a framework, a handle, and a plurality of shelves that are pivotally coupled to a mounting bar and individually rotatable to a plurality of different positions relative to a stop bar.

In some embodiments, the storage system further includes a plurality of cylindrical vial containers that each hold at least one of the products. The side wall of each of the plurality of shelves may define a generally cylindrical shape to allow the container receptacle defined therein to receive one of the cylindrical vial containers. Each vial container includes a main body with a bottom end and a sidewall collectively defining an enclosure for receiving a vial or product, and a lid that removably engages the main body at a threaded engagement with the sidewall. Therefore, access to the vial or product is made easy by the threaded connection between these elements. The storage rack with any other products or samples can then be returned to the outer sleeve element and the cryogenic container for future access and use, but it will be understood that the plurality of shelves must typically be aligned with one another before the storage rack will fit into the rack receptacle defined within the outer sleeve element. The storage system also includes a cryogenic storage container that holds a storage space therein at a desired temperature within a range of about −190° C. to about −120° C.

In a further embodiment of the invention, a method of storing and retrieving products to be maintained at a desired temperature is provided. The method includes placing a storage system within a storage space of a cryogenic storage container that is held at the desired temperature. The storage system includes an outer sleeve element and a storage rack configured to hold the products and inserted into the outer sleeve element. The storage rack is similar to the one described above, e.g., it includes a framework with an elongate mounting bar and a stop bar, a handle, and a plurality of shelves pivotally coupled to the mounting bar. The method also includes removing the storage rack from the outer sleeve element and from the cryogenic storage container by engaging the gripping portion of the handle, which extends between the stop bar and the mounting bar. One shelf is then rotated away from engagement with the stop bar to put the one shelf out of alignment from a remainder of the plurality of shelves. This rotation of the one shelf provides access to one of the products that is stored at the one shelf. The retrieval of products is made quick and easy by this configuration of the storage system and storage rack, as a user can grab and manipulate the storage rack with one hand on the handle, while using another hand to move the one shelf and a product on the one shelf. As such, thermal-induced degradation of other samples on the storage rack can be more readily avoided when performing the method of the invention described herein.

These and other objects and advantages of the invention will become more readily apparent during the following detailed description taken in conjunction with the drawings herein.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

DETAILED DESCRIPTION

With reference to the Figures, and more specifically to FIGS. 2 through 7, an exemplary storage system 10 including a storage rack 12 is illustrated, according to one embodiment of the invention. The storage system 10 is configured to be received within a cryogenic storage container such that products or samples stored on the storage rack 12 are maintained at a desired temperature, such as at a cryogenic temperature range of about −190° C. to about −120° C. The storage rack 12 is designed to make manipulation and movement of the storage rack 12, shelves and containers on the storage rack 12 quick and easy, even for users without significant experience working with the storage rack 12. Accordingly, other product samples on the storage rack can be reliably returned to the cryogenic environment quickly to avoid thermal-inducted degradation of samples. The storage rack 12 therefore improves upon prior storage rack designs by addressing several of the shortfalls of such conventional designs, including the one described above in the Background section of this application (storage rack 300).

Figure 2:
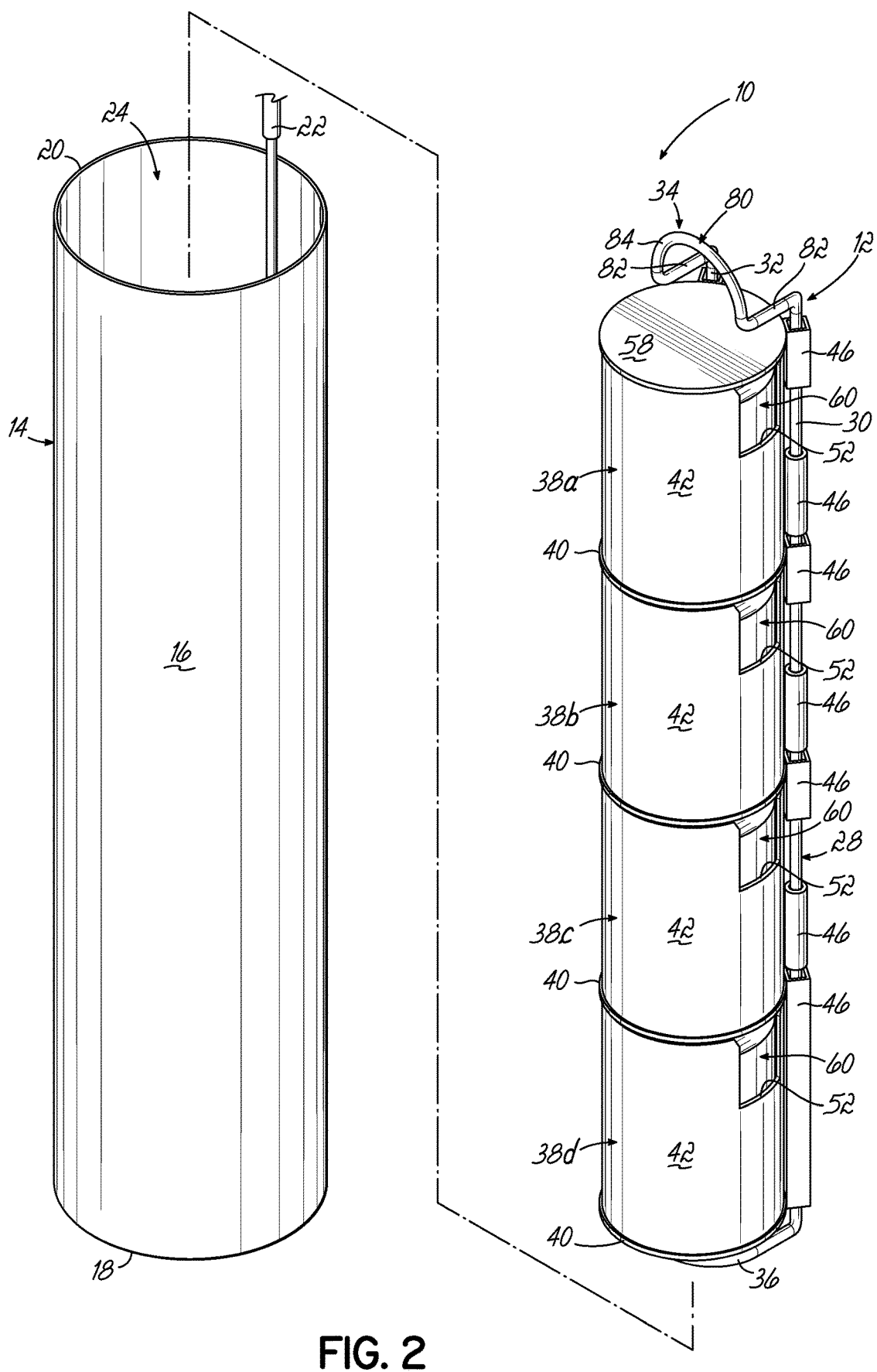
FIG. 2 is a top perspective view of a storage system including a storage rack and a storage sleeve configured to position the storage rack within a cryogenic storage container, in accordance with one embodiment of the invention, the storage rack being shown to be separated from the storage sleeve with all shelves aligned against a stop bar.

As shown in FIG. 2, the storage system 10 of this embodiment includes an outer sleeve element 14 and the storage rack 12, which is configured to be inserted into the outer sleeve element 14 for storage in a cryogenic storage container or other similar refrigerated space. The outer sleeve element 14 is generally tube-shaped and includes a cylindrical sidewall 16 extending between a closed bottom end 18 (may be a wall that is solid or perforated) and an open top end 20. The outer sleeve element 14 typically further includes a handle rod 22 that is fixedly coupled to the sidewall 16 proximate the open top end 20 and that projects upwardly above the open top end 20 so that the outer sleeve element 14 can be moved and manipulated by a user. In an exemplary embodiment, the outer sleeve element 14 is formed from a rigid metal material such as stainless steel (e.g., 304 SS or 316 SS), but it will be appreciated that other types of materials appropriate for use in cryogenic temperature environments may also be used.

The sidewall 16 and closed bottom end 18 of the outer sleeve element 14 enclose a rack receptacle 24, which is a generally cylindrical interior space sized to receive the storage rack 12, at least when the storage rack 12 is in the configuration shown in FIG. 2. To this end, the rack receptacle 24 may be sized only slightly larger than the storage rack 12 to help maintain the aligned configuration of the storage rack 12 after insertion into the outer sleeve element 14. The outer sleeve element 14 can then be moved with the storage rack 12 by a user to and from the cryogenic storage. It will be understood that the particular shape and size of the outer sleeve element 14 may be modified in other embodiments to match corresponding revisions that may be made in the shape or design of the storage rack 12, without departing from the scope of the invention.

Figure 3:
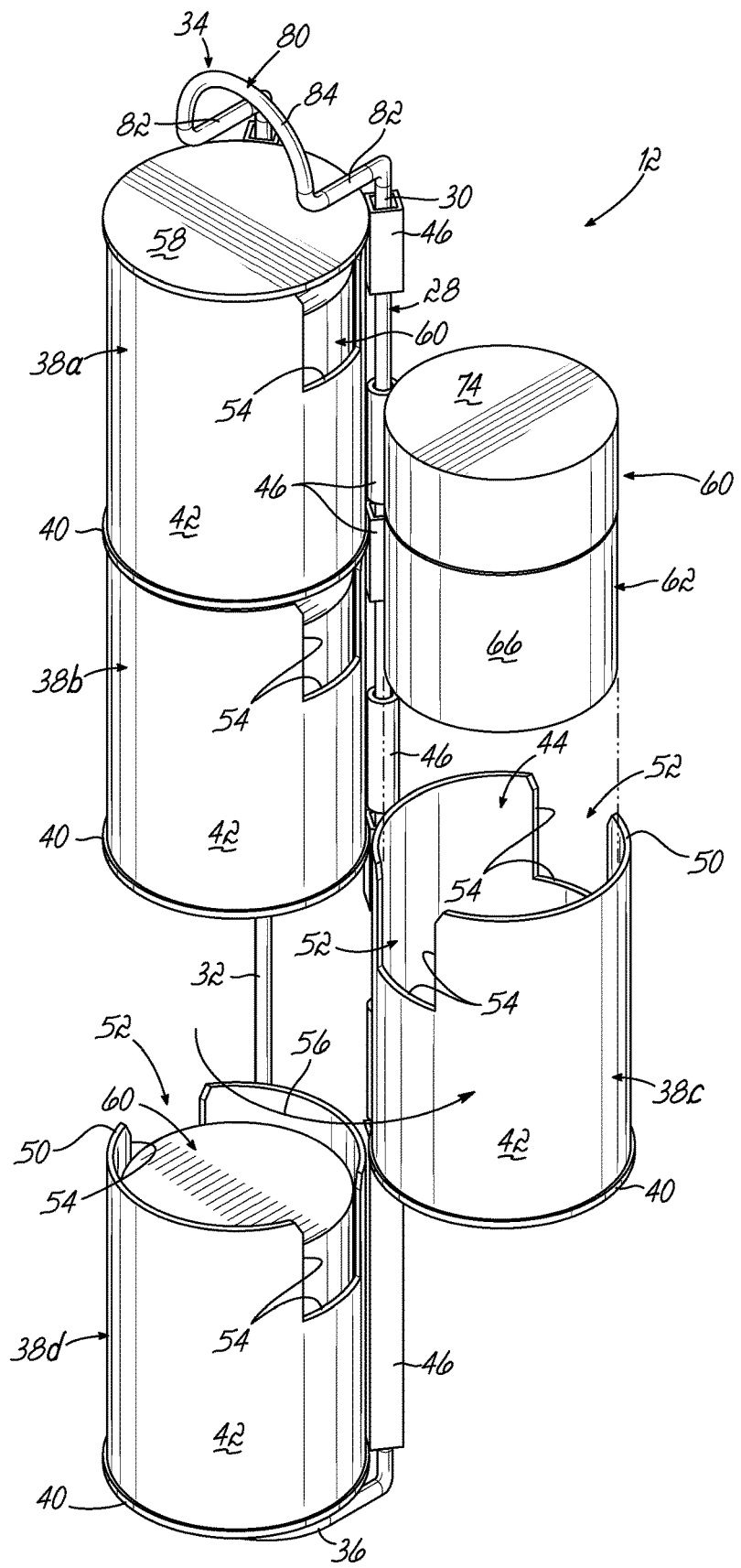
FIG. 3 is a top perspective view of the storage rack of FIG. 2, but with one of the shelves rotated to an accessible position such that a round product container (shown lifted out of the shelf) may be retrieved from the storage rack.

The storage rack 12 of this embodiment is shown in further detail in FIGS. 2 and 3. In this regard, the storage rack 12 includes a framework 28 defined by an elongate mounting bar 30 and an elongate stop bar 32 that are coupled to one another so as to be in generally parallel relationship. For example, a handle 34 is provided on the storage rack 12 so as to extend between top ends of the mounting bar 30 and the stop bar 32. The handle 34 therefore couples the mounting bar 30 and stop bar 32 together, while providing additional functionality to the storage rack 12 as described in further detail below. Moreover, the framework 28 typically further includes a support foot 36 that is shown connected to and extending from a bottom end of the mounting bar 30 in FIGS. 2 and 3. The support foot 36 may also be connected to and extending from a bottom end of the stop bar 32 in some embodiments, which will provide an additional coupling of these elements together. Additional connecting elements (not shown in this embodiment) may extend between the mounting bar 30 and the stop bar 32 along their length to maintain these elements of the framework 28 in the desirable parallel configuration, in some embodiments. Regardless of how the framework 28 is connected together, the mounting bar 30 and the stop bar 32 provide mounting and alignment functionalities for a plurality of shelves 38 included in the storage rack 12.

The framework 28 in this embodiment is formed from elongated cylindrical rod stock, which may be formed from stainless steel or another similar rigid material configured to provide structural strength and withstand cryogenic environments. The rod stock may be solid in cross section or hollow, depending on the preferences of the end user. The support foot 36 may be formed integrally as a unitary piece with the mounting bar 30 and/or stop bar 32, in which case the support foot 36 is also formed from the same rod stock. However, the support foot 36 may be formed separately and fixedly secured into connection with the mounting bar 30 in other embodiments. Although the shape and profile of the support foot 36 is not visible in FIGS. 2 and 3, it will be understood that the support foot 36 can define a hollow enclosed triangular shape or rectangular shape extending along a plane (which is visible in FIG. 6, for example). Furthermore, the support foot 36 can define any shape and size in other embodiments, so long as the support foot 36 provides sufficient support for holding the storage rack 12 in an upright position on a surface as shown in the different configurations at FIGS. 2 and 3. To this end, in most embodiments, the support foot 36 will extend in some manner across a majority of the footprint of the storage rack 12, defined by the plurality of shelves 38 when in the aligned configuration of FIG. 2, to provide the necessary support for holding the storage rack 12 in the upright position.

Turning with reference to the plurality of shelves 38, the storage rack 12 of the illustrated embodiment includes four shelves 38a, 38b, 38c, 38d (collectively referred to as 38) positioned one immediately above the other. It will be understood that more or fewer shelves, such as up to 12 shelves in some embodiments, may be provided in accordance with this invention. Each of the shelves 38 is defined by a bottom wall 40 extending generally horizontally in the upright position shown in FIGS. 2 and 3, and a side wall 42 extending generally vertically and upwardly from the bottom wall 40. The side wall 42 is generally cylindrical in the illustrated embodiment, but it will be appreciated that a plurality of sidewalls may extend upwardly from the bottom wall 40 in other embodiments of the storage rack 12 consistent with the scope of the present invention. Regardless of the particular configuration and shape of the bottom wall 40 and side wall 42, these components collectively define a container receptacle 44 that is sized to receive a vial container or some other product holding container. Therefore, on the illustrated embodiment of the storage rack 12, the plurality of shelves 38 collectively provide four container receptacles 44 that are each sized to receive a vial container, which enables the storage rack 12 to hold a plurality of product samples for cryogenic storage. In some fields, a partial portion of the vial containers will hold reserve materials, while the other partial portion of the vial containers will hold samples that are to be used for treatment or testing, in the example of the samples being biological cells or the like.

Each of the shelves 38 is pivotally coupled to the mounting bar 30 of the framework 28. For example, in the illustrated embodiment the side wall 42 of each shelf 38 includes one or more hinge sleeves 46 that are connected to an outside surface of the side wall 42. The hinge sleeves 46 are provided in this embodiment as hollow members that are sized to receive the mounting bar 30 in a relatively close fit. To this end, the hinge sleeves 46 may define a hollow opening that is about 0.030 inches to 0.100 inches larger than the cross-sectional size of the rod stock defining the mounting bar 30, which provides a close fit but sufficient clearance to enable the pivotal movement between these elements. The hinge sleeves 46 of adjacent shelves 38 can abut one another (or define sufficiently small gaps therebetween) in some embodiments to prevent significant vertical movement of the shelves 38 along the elongate length of the framework 28. Nevertheless, no further bearing or mounting elements are required in the illustrated embodiment to hold the shelves 38 in position, e.g., with one above the other as shown. Some of the hinge sleeves 46 are shown with a generally square cross section, while others of the hinge sleeves 46 are shown with a generally cylindrical cross section. It will be understood that so long as the clearance gap provided between the hinge sleeves 46 and the mounting bar 30 is sufficient to enable the pivotal movement of the shelves 38, the particular shape and configuration of the hinge sleeves 46 can be further modified in other embodiments.

As with the other elements described above, the shelves 38 and the components defining the same are typically formed from stainless steel, such as 304 SS or 316 SS, or a similar structural, rigid material. When most of the elements of the storage rack 12 and storage system 10 are provided from a stainless steel material, the storage solution has high durability and reliability for many storage cycles. Furthermore, the manufacturing and assembly of the elements of the storage system 10 is straightforward, as it may be performed by known metal shaping and coupling techniques (e.g., welding and the like). The specific materials chosen for the shelves 38 and the other elements of the storage system 10 may be modified without undermining the various benefits and functionalities of this design.

As shown in FIGS. 2 and 3, the side wall 42 of each of the shelves 38 extends to a top end 50 that is positioned at an opposite vertical end from the connection of the side wall 42 to the bottom wall 40. The top end 50 defines an opening into the container receptacle 44 through which the vial containers or other elements stored on the shelves 38 can be retrieved and manipulated. In the exemplary embodiment shown, the side wall 42 further includes at least one cutout 52 projecting downwardly from the top end 50 and towards the bottom wall 40. More specifically, the side wall 42 has a pair of opposing cutouts 52 that are formed generally on opposite sides of the shelf 38. The cutouts 52 are sized to be large enough to receive at least one or two fingers of a user, and they may extend a partial portion (e.g., about 25%-35%) of the longitudinal length of the shelf 38 defined between the top end 50 and the bottom wall 40.

As will be readily understood from FIG. 3, the cutouts 52 provide a convenient gripping area for a user to grab onto the top of a vial container 60 that is to be pulled out of the corresponding container receptacle 44 via the top end 50. While opposing cutouts 52 are shown and allow for a clamp like grip to be formed by a user with only one hand on the vial container 60, it will be understood that a different number of cutouts 52 may be provided on each shelf 38 in other embodiments consistent with the scope of the invention. Moreover, while the cutouts 52 are shown with generally straight edges 54 and a rectangular shape in this embodiment, the particular edge profile of the cutouts 52 may be modified depending on the preferences of the end user of the storage rack 12. When one or more of the shelves 38c is rotated out of alignment with the other shelves 38a, 38b, 38d on the storage rack 12, the cutouts 52 and top end 50 provide open and easy access for removal and/or replacement of a vial container 60 to and from the storage rack 12.

As initially described above, each of the shelves 38 is pivotally coupled to the mounting bar 30 so that the shelves 38 are configured to be individually and independently rotated relative to the mounting bar 30 towards and away from contact with the stop bar 32. In this regard, the stop bar 32 provides a limit on the rotation of any shelf 38 in both directions when pivoting around the periphery of the mounting bar 30, but each shelf 38 is still capable of moving through a swing angle of about 270 degrees or more between end conditions contacting the opposite sides of the stop bar 32. That freedom of rotational movement allows for the plurality of shelves 38 to be repositioned relative to one another in a multitude of different configurations and positions.

One such position is shown in FIG. 2, with all of the shelves 38a, 38b, 38c, 38d rotated into contact with the stop bar 32 and into alignment with one another. The FIG. 2 position is designed for storage within the outer sleeve element 14 and a cryogenic storage container, as the effective footprint of the storage rack 12 is minimized to just the size of one of the shelves 38 (and the mounting bar 30 and stop bar 32 of the framework 28 of course). Another such position is shown in FIG. 3, in which one of the shelves 38c is rotated away (shown by arrow 56) from the remainder and away from the stop bar 32 to move that shelf 38c completely out of alignment with the other shelves 38a, 38b, 38d. As shown by the partially exploded view in FIG. 3, this configuration of the shelves 38 on the storage rack 12 enables access for removal and/or replacement of the vial container 60 to and from the container receptacle 44 defined within the one shelf 38c. To this end, the open top end 50 is revealed along with the cutouts 52 for allowing a user's hand to grasp the top of a vial container 60 within the container receptacle 44. In addition, with the bottom wall 40 of the one shelf 38c rotated away from the top end 50 of the shelf 38d immediately below the one shelf 38c, the open top end 50 and the cutouts 52 of that adjacent shelf 38d are also revealed for access by a user, if desired.

The shelves 38 can therefore be repositioned to provide access to any one or all of the container receptacles 44 in quick and easy manner, as a user can rotate a shelf 38 with one hand and then use the same hand to retrieve the vial container 60 by lifting it out of the corresponding container receptacle 44. The shelves 38 of the storage rack 12 are shown in two exemplary configurations and positions, one for storage, and one providing access into some of the container receptacles 44, but it will be appreciated that many other configurations and shelf positions are also possible when using the storage rack 12 of this invention.

The rotatable configuration of the plurality of shelves 38 also provides another benefit that is visible when comparing the states of FIGS. 2 and 3. To this end, the bottom wall 40 of each of the shelves 38a, 38b, 38c above the lowermost one 38d effectively serves as a lid element for the shelf 38b, 38c, 38d (respectively) located directly below it in sequence, particularly when the shelves 38 are aligned with one another in the storage position as shown in FIG. 2. The shelves 38 are mounted on the mounting bar 30 so that the clearance gaps, if any, between two adjacent shelves 38 in the series are about 0.1 inch or less. The clearance gap is substantially invisible in the side view of FIG. 6, for example. Therefore, no separate lids or wall elements need to be mounted on the framework 28 to cover and close the container receptacles 44 for each of the shelves 38b, 38c, 38d except for the uppermost one 38a, and this simplifies and reduces cost of manufacturing the storage rack 12 while maintaining reliable retention of vial containers 60 in the substantially closed container receptacles 44 (when in the aligned storage position). It will be appreciated that the storage rack 12 in other embodiments in accordance with the invention may further include one or more additional lid elements mounted to the framework 28 between the shelves 38, but it is preferable to use the bottom walls 40 for such a function as shown in the drawings.

The uppermost of the plurality of shelves 38a on the storage rack 12 does not have an adjacent shelf with a bottom wall that can serve as a lid element in the storage position. As a result, in the exemplary embodiment of the storage rack shown in the Figures, a separate lid element 58 is fixedly coupled to one or both of the mounting bar 30 and the stop bar 32 at a position adjacent the top end 50 of the uppermost one of the shelves 38a. The lid element 58 is configured as a planar round plate in the embodiment shown in FIGS. 2 and 3, although the particular shape of the lid element 58 could be modified in other embodiments so as to be consistent with any variations in the cross-section of the shelves 38. Consequently, the lid element 58 is configured to be similar to the bottom wall 40 of the other shelves 38, just without being rotatable relative to the mounting bar 30 and without the side wall 42 extending further upwardly from the lid element 58. It will be appreciated that the lid element 58 could be omitted in some embodiments in which closure of the container receptacles 44 is not required, as the shelves 38 are adapted to reliably retain the vial containers 60, regardless of whether a lid element is provided.

Figure 4:
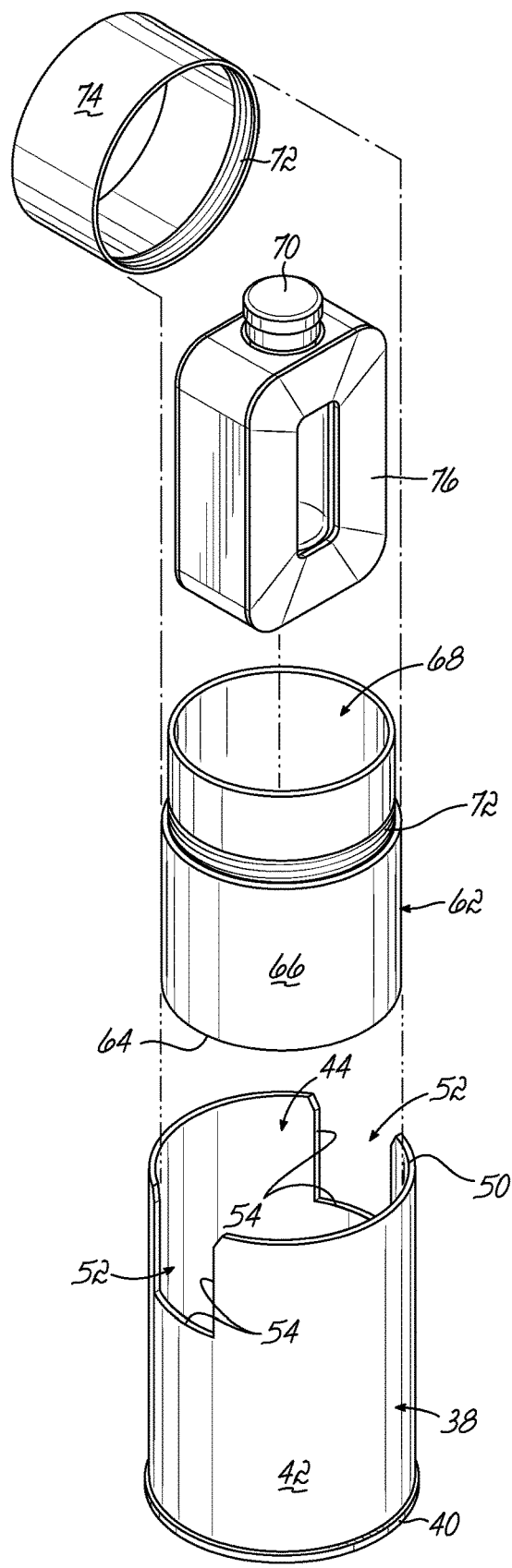
FIG. 4 is a partially exploded top perspective view of the shelf and round product container of FIG. 3, showing additional details of the round product container as well as a vial packing located within the round product container.

The vial container 60 developed for use with the storage system 10 of this invention is shown in further detail in FIGS. 3 and 4. In this regard, the vial container 60 is a cylindrical vial container in this embodiment so that the vial container 60 fits within the generally cylindrical space defined by the container receptacles 44 of the plurality of shelves 38. Each of the vial containers 60 is sized to hold at least one sample or product, which may include, but is not limited to: biological samples such as tissue samples or stem cells, allogeneic drug products, and autologous drug products, for example. As these types of products and samples typically require continuous storage at cryogenic temperatures of −120° C. or less, the ease and speed with which a user can retrieve one of the samples and then return any others on the shelf 38 or storage rack 12 back to cryogenic storage is important in this field, so as to avoid temperature-induced degradation of the other samples on the storage rack 12. The vial container 60 has been designed with those needs being considered.

For example, by making the vial container 60 generally cylindrical, the mechanism for opening the vial container 60 can be redesigned to use a rotatable threaded engagement rather than flaps and panels ("box ears") that must be bent open and closed as with conventional plastic or cardboard box-shaped designs. To this end, each of the vial containers 60 shown in the storage system 10 of this embodiment includes a main body 62 defined by a bottom end 64 and a sidewall 66 that collectively enclose an enclosure 68 configured to receive a vial 70 containing the sample or product. The sidewall 66 on the main body 62 includes threads 72 which may be engaged with corresponding threads 72 formed on a lid 74 that removably engages with the main body 62 to open and close the enclosure 68. The sidewall 66 on the main body 62 may be recessed to be slightly smaller in cross section near a top end so that the lid 74 (specifically a sidewall thereof) can slide down over this portion of the sidewall 66, which allows the lid 74 and the main body 62 to provide a generally uniform profile when fully assembled. Regardless, the lid 74 can be removed and replaced relative to the main body 62 of the vial container 60 in a quick and intuitive manner, even for users not highly experienced with this particular storage system 10 design.

The vial container 60 may be formed from a plastic material or another similar material. The vial 70 containing the sample or product is often significantly smaller in size than the enclosure 68 defined within vial container 60, and as such, the vial 70 may optionally be further contained within a holder 76 that is sized to span the gap between the vial 70 and the sidewall 66 defining the enclosure 68. The holder 76 is shown as a cardboard or plastic box-shaped element with an outer profile sized to fit just within the enclosure 68, and an inner chamber or sleeve sized to receive the vial 70. The holder 76 maintains the position of the vial 70 within the enclosure 68 so as to avoid undesirable jostling or impacts of the vial 70 moving around inside the shelves 38 during movement and manipulation of the shelves 38 and/or of the storage rack 12 in its entirety. The holder 76 may be designed to hold more than one vial 70, or different shapes and sizes of vials, in other embodiments of the invention.

Figure 5:
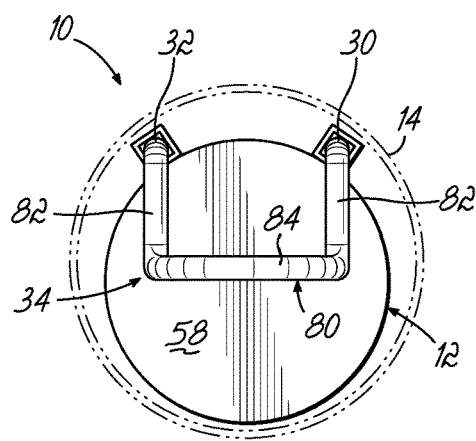
FIG. 5 is a top view of the storage rack of FIG. 2, with all shelves being aligned such that the storage rack can be inserted back into the storage sleeve, which is shown in phantom for reference.
Figure 6:
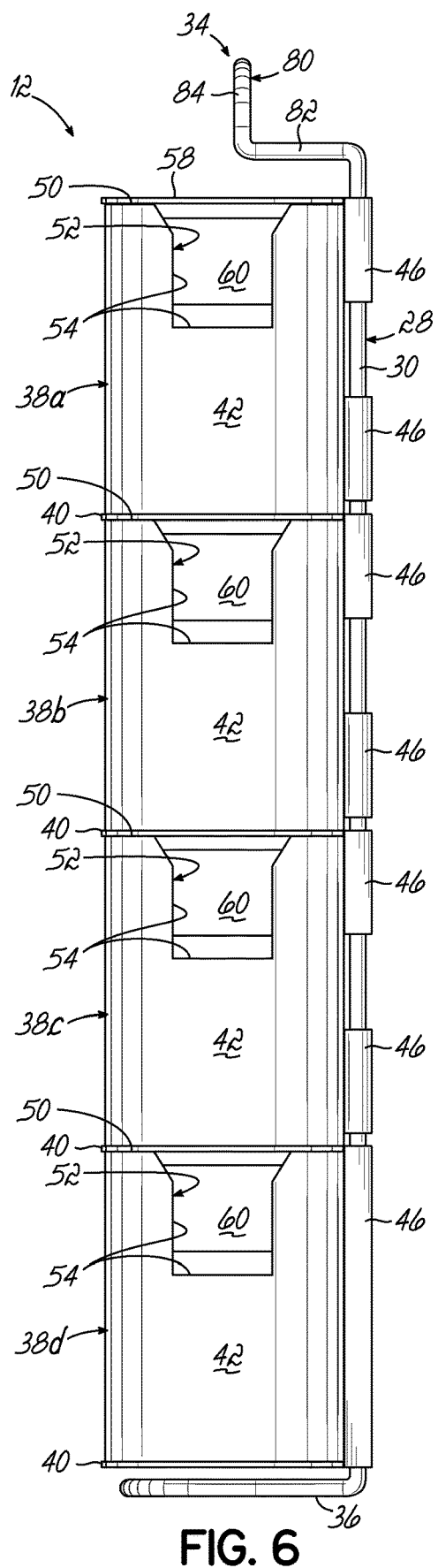
FIG. 6 is a side view of the storage rack of FIG. 2.

Turning now with reference to FIGS. 5 and 6, the storage rack 12 is shown from multiple sides while in the aligned position of the shelves 38 to illustrate further features. For example, the specific positioning and profile of the handle 34 on the storage rack 12 is shown in further detail. The handle 34 of this embodiment is connected to and extends between the mounting bar 30 and stop bar 32 as described above. The handle 34 may be formed integrally as a unitary piece from a similar stainless steel rod stock as the mounting bar 30 and the stop bar 32, for example. The handle 34 is bent and profiled in such a manner to provide an enlarged gripping area 80 for a user to hold when moving and manipulating the storage rack 12. This enlarged gripping area 80 is conveniently located so that movements of the storage rack 12 as a whole are made easy relative to the outer sleeve element 14 and/or a cryogenic storage container.

Figure 1:
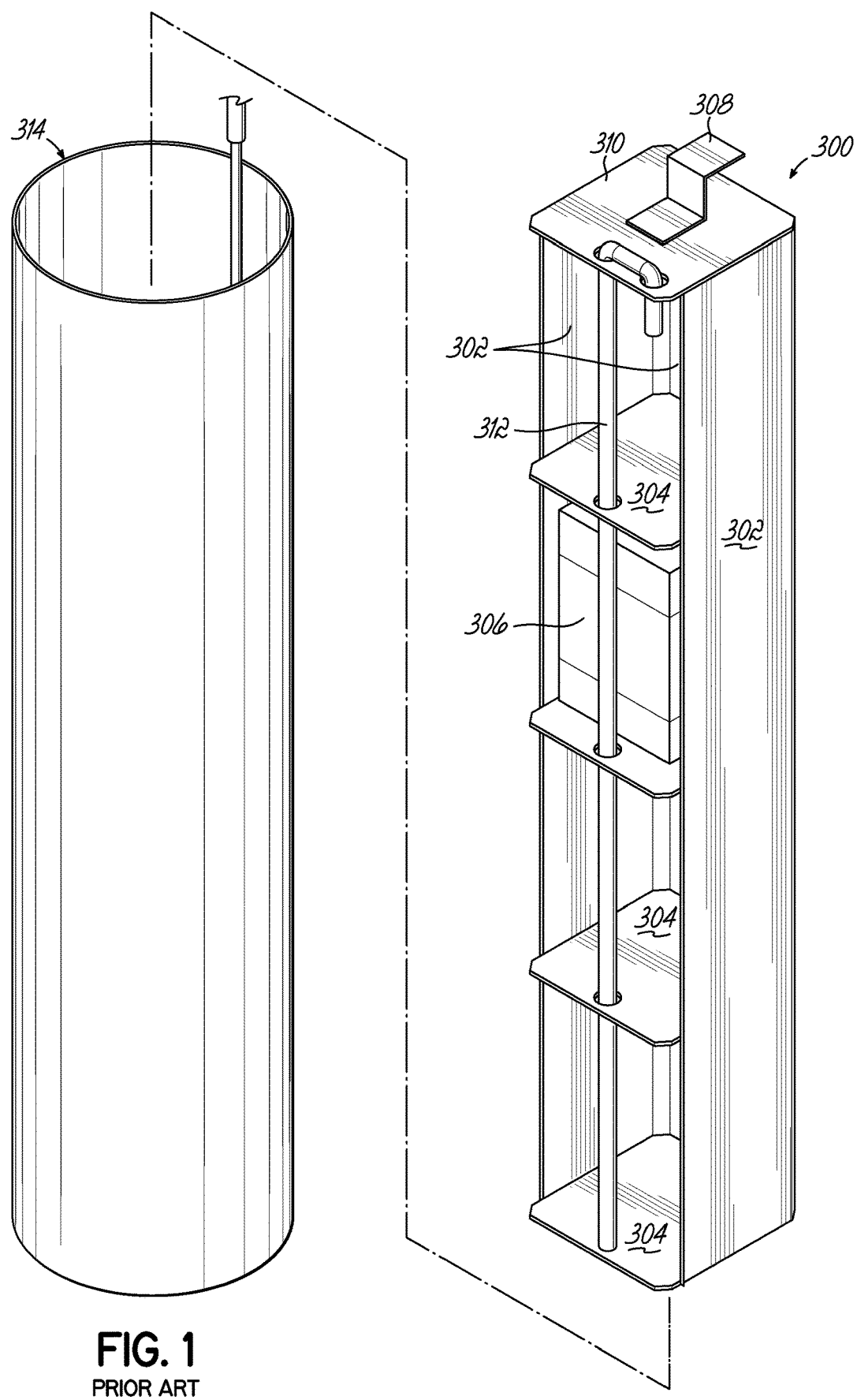
FIG. 1 is a top perspective view of a storage system including a conventional storage rack and a storage sleeve configured to position the storage rack within a cryogenic storage container, the storage rack being separated from the storage sleeve to reveal additional features.

More particularly, the handle 34 as shown in FIGS. 5 and 6 projects both horizontally and upwardly from the top ends of the stop bar 32 and the mounting bar 30. The handle 34 includes generally straight portions 82 extending generally horizontally and perpendicular to the top ends of the stop bar 32 and the mounting bar 30, in a direction over the shelves 38 when the shelves 38 are in the aligned storage position. The handle 34 also includes a generally arcuate portion 84 that extends in a vertical plane from the ends of the generally straight portions 82 opposite the top ends of the mounting bar 30 and the stop bar 32. The generally arcuate portion 84 follows a semi-circular path between the connections with the straight portions 82 of the handle 34. Thus, the arcuate portion 84 of the handle 34 extends over the shelves 38 at roughly the center of the shelves 38, as most visible in FIG. 5, and the arcuate portion 84 defines the curved configuration to provide the gripping area 80. As compared to straight rod-like handles or the small clip handle shown in the prior art design discussed with reference to FIG. 1 above, the enlarged gripping area 80 on the handle 34 enables easy movement and manipulation of the entire storage rack 12 with just one hand of a user. Accordingly, a user has another hand free to conduct the manipulation of the shelves 38 and access of the vial containers 60. The specific curvature and profile of the handle 34 may be modified in other embodiments, as long as the enlarged gripping area 80 is still provided to make the storage rack 12 easier to work with and manipulate, to enable quick retrieval of products or samples and thereby avoid temperature-induced degradations of other products or samples on the storage rack 12.

By providing the storage system 10 and storage rack 12 with the features described herein, users of all experience levels can quickly and easily retrieve and return products and samples to and from a cryogenic storage environment. The enlarged gripping area 80 of the handle 34 renders the storage rack 12 easy to grasp and manipulate relative to the outer sleeve element 14, for example. The rotatable plurality of shelves 38 then makes it simple for the user to move a shelf 38 to an accessible position out of alignment with the other shelves 38, such that a vial container 60 can be moved into or out of the container receptacle 44 at the shelf 38. The vial container 60 itself is also configured to be easy to use, with the threaded engagement of the lid 74 making it easy to open the enclosure 68 and access the vial 70 containing the product or sample. These elements of the storage rack 12 are easy to access, disassemble, and re-assemble to limit the exposure time to ambient temperatures for all other products and samples stored on the storage rack 12. Consequently, the storage system 10 and storage rack 12 is easier for all users of all experience levels to work with, while also reducing the time needed for accessing products and samples to avoid thermal degradation issues.

Figure 7:
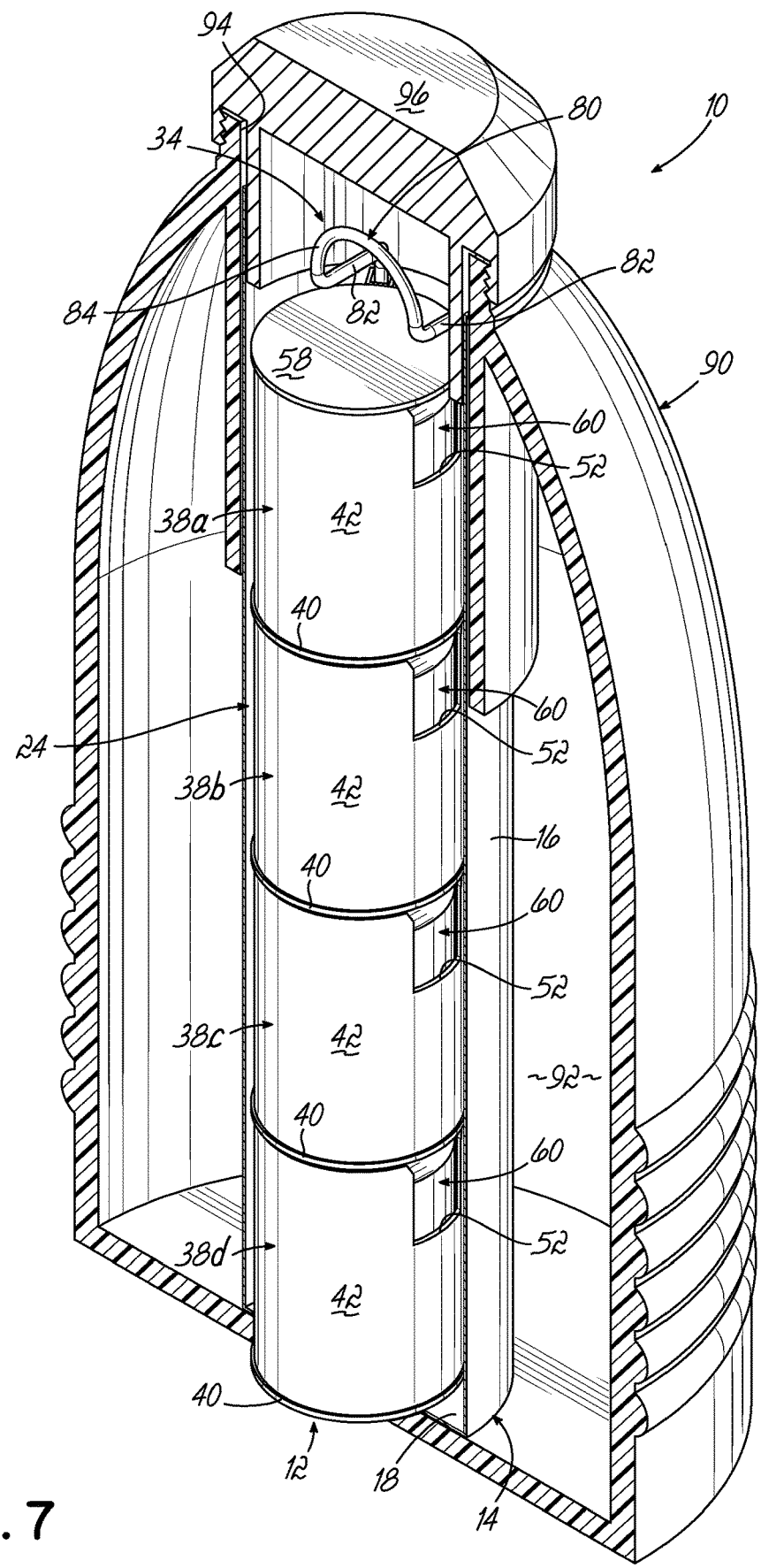
FIG. 7 is a partially cross-sectioned perspective view of the storage rack and storage sleeve of FIG. 2 positioned within a cryogenic storage tank.

One typical environment in which the storage rack 12 is stored is a cryogenic storage tank 90 configured for shipping and transport between locations, as shown in FIG. 7. To this end, the storage system 10 in some embodiments includes the cryogenic storage tank 90, or some other similar cooling enclosure configured to hold elements at a low desired temperature such as in the range of $-195°$ C. to about $-120°$ C. The cryogenic storage tank 90 is a known type of enclosure which typically contains liquid nitrogen (LN2) as a coolant for holding the temperature within an interior 92 of the tank 90 at the low cryogenic temperature. The tank 90 also includes a top opening 94 that can be closed by a cap member 96 that threadably engages with the tank 90. The cap member 96 and the walls of the tank 90 are insulated with foam material or similar to help maintain the cryogenic temperatures within the interior 92. The tank 90 shown in FIG. 7 is sized so as to receive a single storage rack 12, placed within the outer sleeve element 14 as described previously. As can be seen in FIG. 7, the handle 34 is conveniently positioned such that when the cap member 96 is removed, the handle 34 is located for easy access to allow movement of the storage rack 12 upwardly and out of the cryogenic storage tank 90. It will be understood that the specific cryogenic storage container used with the storage system 10 can be modified to other known designs, some of which may contain multiple storage racks 12, without departing from the scope of this invention.

While the present invention has been illustrated by a description of an exemplary embodiment and while this embodiment has been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and method, and illustrative example shown and described. Accordingly, departures may be made from such details without departing from the scope of Applicant's general inventive concept.

What is claimed is:

1. A storage rack for retaining products in a cryogenic environment, comprising:
   a framework including an elongate mounting bar and an elongate stop bar coupled to one another, the stop bar spaced apart from and extending generally parallel to the mounting bar;
   a handle coupled to at least one of the stop bar and the mounting bar, the handle configured to enable movement of the storage rack as a whole; and
   a plurality of shelves each pivotally coupled to the mounting bar so as to be individually and independently rotatable relative to an axis through the mounting bar towards and away from contact with the stop bar, the stop bar providing a limit on rotation of each shelf of the plurality of shelves in both directions such that each shelf can freely rotate to a multitude of different positions between end positions defined by shelf contact with opposite sides of the stop bar, each of the plurality of shelves including a bottom wall and a side wall collectively defining a container receptacle, wherein rotating all of the plurality of shelves into contact with one side of the stop bar causes the plurality of shelves to be aligned for storage.

2. The storage rack of claim 1, wherein each of the plurality of shelves is configured to be rotated away from the stop bar and out of alignment with others of the plurality of shelves to provide access into the container receptacle defined within the one of the plurality of shelves.

3. The storage rack of claim 1, wherein the side wall of each of the plurality of shelves defines a generally cylindrical shape, thereby making the container receptacles configured to receive a cylindrical vial container holding one of the products.

4. The storage rack of claim 3, wherein the side wall of each of the plurality of shelves further comprises:
   a top end positioned opposite the bottom wall; and
   at least one cutout extending downwardly towards the bottom wall provided at the top end.

5. The storage rack of claim 4, wherein the at least one cutout comprises:
   a pair of opposing cutouts formed on opposite sides of the side wall at the top end thereof, the pair of opposing cutouts providing access to grip and lift the cylindrical vial container out of the container receptacle.

6. The storage rack of claim 1, wherein the handle is coupled to both of the stop bar and the mounting bar, with the handle extending between the stop bar and the mounting bar to provide an enlarged gripping area for moving and manipulating the storage rack.

7. The storage rack of claim 6, wherein the handle projects horizontally and upwardly from top ends of the stop bar and the mounting bar to project over a portion of the plurality of shelves.

8. The storage rack of claim 7, wherein the handle defines a curved configuration to define the gripping area.

9. The storage rack of claim 1, wherein the side wall of each of the plurality of shelves further includes a top end positioned opposite the bottom wall, and the storage rack further comprises:
   a lid element fixedly coupled to at least one of the mounting bar and the stop bar at a position adjacent the top end of an uppermost one of the plurality of shelves when the uppermost one of the plurality of shelves is rotated into contact with the stop bar, the lid element thereby covering the container receptacle of the uppermost one of the plurality of shelves,
   wherein the bottom wall of each of the plurality of shelves also serves as a lid element for an adjacent one of the plurality of shelves located immediately below the bottom wall.

10. The storage rack of claim 9, wherein the lid element and the plurality of shelves define clearance gaps between one another of 0.1 inch or less.

11. The storage rack of claim 1, wherein the plurality of shelves includes at least four shelves pivotally coupled to the mounting bar.

12. The storage rack of claim 1, wherein the handle is connected to a top end of at least one of the stop bar and the mounting bar,
   the framework further comprises a support foot connected to a bottom end of at least one of the stop bar and the mounting bar, so as to be on an opposite end of the framework from the handle, and
   the framework is defined by only the stop bar and the mounting bar between the handle and the support foot.

13. A storage system for retaining products in a cryogenic environment, comprising:

an outer sleeve element sized to be received in a cryogenic chamber; and
a storage rack configured to hold the products and configured to be inserted into the outer sleeve element during placement in the cryogenic chamber, the storage rack comprising:
   a framework including an elongate mounting bar and an elongate stop bar coupled to one another, the stop bar spaced apart from and extending generally parallel to the mounting bar;
   a handle coupled to at least one of the stop bar and the mounting bar, the handle configured to enable movement of the storage rack as a whole; and
   a plurality of shelves each pivotally coupled to the mounting bar so as to be individually and independently rotatable relative to an axis through the mounting bar towards and away from contact with the stop bar, the stop bar providing a limit on rotation of each shelf of the plurality of shelves in both directions such that each shelf can freely rotate to a multitude of different positions between end positions defined by shelf contact with opposite sides of the stop bar, each of the plurality of shelves including a bottom wall and a side wall collectively defining a container receptacle,
wherein rotating all of the plurality of shelves into contact with one side of the stop bar causes the plurality of shelves to be aligned for storage.

14. The storage system of claim 13, wherein the side wall of each of the plurality of shelves defines a generally cylindrical shape, and the storage system further comprises:
   a plurality of cylindrical vial containers each holding one of the products, and each positioned within a corresponding one of the container receptacles.

15. The storage system of claim 14, wherein each of the plurality of cylindrical vial containers further comprises:
   a main body having a bottom end and a sidewall collectively defining an enclosure for receiving a vial containing one of the products; and
   a lid that removably engages the main body at a threaded engagement with the sidewall of the main body to open and close access to the vial within the enclosure.

16. The storage system of claim 13, wherein the outer sleeve element defines a rack receptacle sized to receive the storage rack only when all of the plurality of shelves are aligned by being rotated into contact with the stop bar.

17. The storage system of claim 13, wherein the handle is coupled to both of the stop bar and the mounting bar, with the handle extending between the stop bar and the mounting bar to provide an enlarged gripping area for moving and manipulating the storage rack relative to the outer sleeve element.

18. The storage system of claim 17, wherein the handle projects horizontally and upwardly from top ends of the stop bar and the mounting bar to project over a portion of the plurality of shelves, and wherein the handle defines a curved configuration to define the gripping area.

19. The storage system of claim 13, further comprising:
   a cryogenic storage container enclosing a storage space held at a desired temperature within a range of about $-195°$ C. to about $-120°$ C., wherein the storage rack and the outer sleeve element are inserted into the cryogenic storage container for transport at the desired temperature.

20. The storage system of claim 13, wherein the handle is connected to a top end of at least one of the stop bar and the mounting bar, the framework further comprises a support foot connected to a bottom end of at least one of the stop bar and the mounting bar, so as to be on an opposite end of the framework from the handle, and the framework is defined by only the stop bar and the mounting bar between the handle and the support foot.

* * * * *